(12) United States Patent
Denes et al.

(10) Patent No.: US 7,536,975 B2
(45) Date of Patent: May 26, 2009

(54) PLASMA-ASSISTED DISINFECTION OF MILKING MACHINES

(75) Inventors: Ferencz S. Denes, Madison, WI (US); Douglas J. Reinemann, Madison, WI (US); Sorin O. Manolache, Madison, WI (US); Jason M. Helgren, Beaver Dam, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 647 days.

(21) Appl. No.: 10/921,551

(22) Filed: Aug. 18, 2004

(65) Prior Publication Data

US 2006/0037542 A1 Feb. 23, 2006

(51) Int. Cl.
*A01J 5/00* (2006.01)

(52) U.S. Cl. .................. 119/14.47; 119/14.18; 119/651

(58) Field of Classification Search ............. 119/14.47, 119/14.53, 14.01, 14.02, 14.18, 650, 651, 119/670; 422/22, 29, 186.04
See application file for complete search history.

(56) References Cited

U.S. PATENT DOCUMENTS

| | | | |
|---|---|---|---|
| 3,934,550 A * | 1/1976 | Worstorff ................. | 119/14.02 |
| 4,244,712 A | 1/1981 | Tongret | |
| 4,452,176 A * | 6/1984 | Hoefelmayr et al. ..... | 119/14.17 |
| 5,326,530 A | 7/1994 | Bridges | |
| 5,843,288 A | 12/1998 | Yamamoto | |
| 5,876,663 A | 3/1999 | Laroussi | |
| 5,895,558 A | 4/1999 | Spence | |
| 6,096,564 A | 8/2000 | Denes et al. | |
| 6,228,330 B1 | 5/2001 | Herrmann et al. | |
| 6,427,624 B1 | 8/2002 | Briggs et al. | |
| 6,488,948 B1 * | 12/2002 | Danieli ..................... | 424/404 |
| 6,543,460 B1 | 4/2003 | Denes et al. | |
| 6,562,386 B2 | 5/2003 | Ruan et al. | |
| 6,588,364 B1 | 7/2003 | Petterson | |
| 6,722,310 B1 | 4/2004 | Älveby et al. | |
| 6,749,759 B2 | 6/2004 | Denes et al. | |
| 6,911,225 B2 | 6/2005 | Ruan et al. | |
| 2003/0129107 A1 | 7/2003 | Denes et al. | |
| 2003/0168009 A1 | 9/2003 | Denes et al. | |
| 2004/0131524 A1 * | 7/2004 | Josephson et al. ....... | 423/240 R |

FOREIGN PATENT DOCUMENTS

| | | |
|---|---|---|
| EP | 0819388 A1 | 1/1998 |
| WO | WO 99/38374 A1 | 8/1999 |
| WO | WO 00/01224 A1 | 1/2000 |

\* cited by examiner

*Primary Examiner*—T. Nguyen
(74) *Attorney, Agent, or Firm*—Craig A. Fieschko, Esq.; DeWitt Ross & Stevens S.C.

(57) ABSTRACT

In a milking machine teat cup wherein an animal to be milked has its teat inserted into a teat cup liner during milking, a first electrode extends about or within at least a portion of the teat cup liner. To clean and/or disinfect the liner, a second electrode is inserted into the liner and the two electrodes are charged so as to generate plasma in any free space between the inserted second electrode and the interior surface of the liner. The generated plasma species destroy organisms that cause mastitis, and can additionally kill other unwanted organisms and/or perform cleaning of the liner's interior.

25 Claims, 1 Drawing Sheet

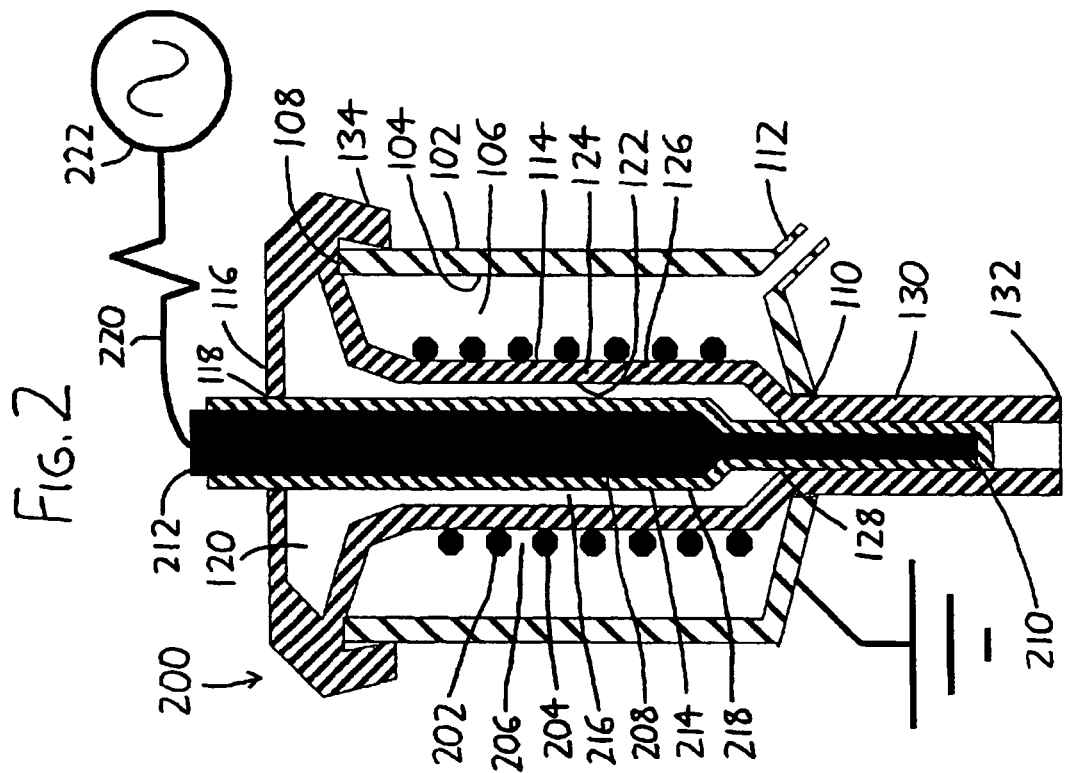
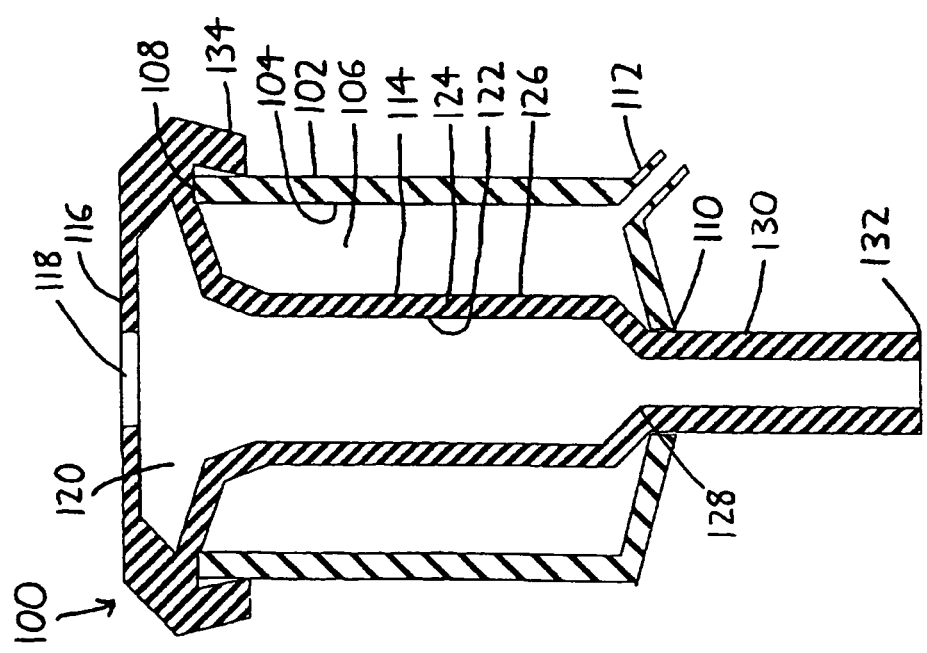
FIG. 1 (PRIOR ART)
FIG. 2

US 7,536,975 B2

PLASMA-ASSISTED DISINFECTION OF MILKING MACHINES

STATEMENT REGARDING FEDERALLY SPONSORED RESEARCH

This invention was made with United States government support awarded by the following agencies:

| USDA/CSREES Grant No(s).: | 2004-35201-14121 |

The United States has certain rights in this invention.

FIELD OF THE INVENTION

This document concerns an invention relating generally to milking machines, and more specifically to methods and apparata for cleaning and sanitizing milking machine teat cup liners.

BACKGROUND OF THE INVENTION

A cross-sectional view of a milking machine teat cup of the type commonly used in the dairy industry is depicted in schematic form in FIG. 1, and is generally denoted by the reference numeral 100. The teat cup 100 includes a teat cup shell 102, which is usually made of a rigid material such as stainless steel or plastic, and which has a generally cylindrical teat cup interior surface 104 surrounding a pulsation chamber 106. The teat cup shell 102 extends between an open teat cup mouth 108 (through which a cow's teat is received as discussed below) and an open milk extraction end 110 (from which milk is extracted). The teat cup shell 102 also generally includes a pressure supply connection nipple 112 which opens onto the pulsation chamber 106 for purposes to be discussed below.

A teat cup liner 114, which is usually formed of rubber or another elastomeric substance, is then mounted under tension within the teat cup shell 102. The teat cup liner 114 has a liner mouth end 116 with a liner mouth 118 sized to receive the cow's teat. The liner mouth 118 opens onto a generally cylindrical liner interior 120, which is surrounded by the interior surface 122 of a barrel portion 124 of the liner 114. The exterior surface 126 of the liner barrel 124 is spaced from the teat cup interior surface 104. The liner barrel 124 radially constricts at the liner barrel exit 128, from which extends a narrower milk line 130 (which may be integrally connected to the barrel exit 128, and which may terminate at a juncture 132 for connection to a "claw" or other milk receiving vessel). It should be understood that the teat cup 100 is usually provided in a milking cluster with three additional teat cups 100, all of which are connected to the claw or other vessel.

During milking, the cow's teat is inserted into the liner mouth 118 to extend down the liner barrel 124. Negative pressure (i.e., a vacuum force) is applied to the liner interior 120 via the milk line 130, and also to the pulsation chamber 106 via the pressure supply connection nipple 112. Milk is thereby extracted from the teat owing to the pressure difference across the orifice of the cow's teat, and the milk is collected through the milk line 130. The pulsation chamber 106 is usually periodically opened to atmospheric pressure (generally about once per second) to cause the liner barrel 124 to collapse, thereby generating a massaging action on the teat from the contracting liner barrel 124. Further examples of teat cups of this nature, and further details on their operation, may be found (for example) in U.S. Pat. No. 6,427,624 to Briggs et al.; U.S. Pat. No. 6,588,364 to Petterson; and U.S. Pat. No. 6,722,310 to Alveby et al., among others.

Since the teat cup liner 114 will eventually wear and/or become unsanitary, it is provided as a removable/disposable component of the teat cup shell 102. For ease of fitting and removal within the teat cup shell 102, the teat cup liner 114 is often provided with a descending flange 134 about its mouth end 116 so that the flange 134 may fit about and affix to the teat cup mouth 108, with the liner milk line 130 fitting through the teat cup extraction end 110.

When using a typical milking machine which includes teat cups such as the teat cup 100, dairy producers are faced with the challenge of preventing the transmission of organisms that cause bovine mastitis, an inflammation of a cow's mammary glands. A mild case of mastitis in a cow can merely reduce milk production, while in a severe case, it may result in the death of the cow. Some of the organisms which cause mastitis are highly contagious, and are easily spread from cow to cow when a milking machine is transferred from one cow to another during milking. Thus, a mastitis outbreak can rapidly spread through a herd and devastate its milk production. One study has estimated the cost of mastitis in the United States to be approximately 6% of the value of milk production (Wells et al., "What Is the Current Milk Quality in the U.S.?," 1998 National Mastitis Council Annual Meeting Proceedings).

Proper sanitation of milking machines is therefore critical to mastitis control. Milking machines are typically cleaned using hot water, detergents, and disinfectants two or three times per day, corresponding to the milking frequency of the herd, so that the machines will theoretically be free of the organisms that cause mastitis. However, since milking machines are rarely cleaned between milking individual cows, mastitis-causing organisms can be easily transferred between cows during a milking session. Devices which clean teat cups 100 between the milking of individual cows have been developed, the most common of which are "backflush" rinsing systems. These have not been widely adopted because they are expensive to install and maintain, and they require large amounts of water and disinfectants for operation. Additionally, they are not always effective in removing bacteria populations from the teat cup liner 114. As a result, it would be beneficial to have a more effective and economical means for quickly and easily disinfecting teat cup liners 114 between milking individual cows, with little or no use of disinfectants or other consumables.

SUMMARY OF THE INVENTION

The invention, which is defined by the claims set forth at the end of this document, is directed to devices and methods which at least partially alleviate the aforementioned problems. A basic understanding of the invention can be attained from a review of the following brief summary of a preferred version of the invention, with more details being provided elsewhere in this document. To enhance the reader's understanding, reference is made to FIG. 2 of this document, wherein a preferred version of the invention is illustrated.

The invention can be implemented in a standard milking machine of the type having a teat cup shell 102 which is equipped to receive an insertable teat cup liner 114, with the teat cup shell 102 having a pressure supply 112 (e.g., a vacuum) which acts on the exterior of the liner barrel 124 of the teat cup liner 114 to radially flex it with respect to a cow's teat resting within the interior of the liner barrel 124. The milking machine is adapted to generate "cold" plasma within its teat cup liner 114 so that the plasma will have a cleaning/antimicrobial effect on the interior surface 122 of the liner. Here, it should be understood that "cold" plasma, also known as nonthermal plasma, is plasma wherein a gas and/or vapor is disassociated into its components (e.g., free electrons, ions, free radicals, and neutral particles) under the influence of an electrical field. In effect, the disassociated gas is at low temperature (e.g., standard environmental temperature) but its electrons are effectively at high temperature (i.e., in a state of high kinetic energy). This is differentiated from "hot" plasma, i.e., dissociated gas in thermal equilibrium at high temperatures (~5000 K), which would generally require special handling procedures. The plasma is preferably generated within the teat cup liner 114 by use of dielectric barrier discharge (DBD) arrangements, i.e., arrangements where electrodes spaced by dielectric material are charged by alternating high voltage electrical current to generate a strong electrical field (and "microbursts" of plasma) within an adjacent gas and/or vapor-filled free space (the free space generally being situated between the electrodes). Further details on cold plasmas and DBD plasma generation can be found, for example, in U.S. Patent Appln. Publication 2003-0129107 to Denes et al., as well as in the references cited in the corresponding U.S. Pat. No. 6,764,658.

One possible plasma generation arrangement is to provide a first electrode 202 within the teat cup shell 102, with the first electrode 202 having a body which is configured to conformally receive the exterior surface 126 of the teat cup liner 114. A second electrode 208 is then provided, preferably in the form of an elongated wand-like member which is removably insertable into the interior 120 of the teat cup liner 114. This second electrode 208, which may have its surface sheathed within a dielectric insulator 214, is preferably configured so that it will be maintained in radially inwardly spaced relationship with respect to the interior surface 122 of the liner barrel 124 of the teat cup liner 114 once inserted therein. For example, the second electrode 208 may have a tip end 210 which is sized to be snugly inserted within the milk line 130 provided at the end of the liner barrel 124 of the teat cup liner 114, with such insertion then holding the remainder of the second electrode 208 spaced concentrically inwardly from the interior surface 122 of the liner barrel 124. A power supply 222 is connected to at least one of the first and second electrodes 202 and 208, and is capable of charging at least one of the electrodes to induce them to generate plasma between the electrodes via dielectric barrier discharges. More particularly, the plasma is preferably generated in the free space 216 between the outer surface 218 of the second electrode 208 and the interior surface 122 of the teat cup liner 114, such that the plasma acts to disinfect the liner's interior surface 122.

Thus, after the milking machine is used to milk a cow, it may be disinfected by removing the cow's teat from the teat cup shell 102 and its liner 114, inserting the second electrode 208 within the liner 114, and activating the power supply 222 to cause plasma generation about the liner's interior surface 122 to disinfect it. After sufficient time has passed for a desired degree of disinfection to occur, the second electrode 208 may be removed from the liner 114, and the milking machine may proceed for use on the next cow within the herd. The arrangement does not require significant time for disinfection, nor does it require the use of chemicals or other consumables. Additionally, it is easily implemented within the structures of conventional milking machines, particularly if the first electrode 202 serves as a ground electrode (in which case it does not bear a charge, and thus little or no wiring is required on the teat cup shell 102). In milking machines which rely on pneumatic stimulation of the teat, the first electrode may be formed in sections 204 (e.g., windings) with apertures or spaces 206 defined therebetween so that any pumping pressure supplied by the pressure supply 112 can be communicated through the first electrode 202 to the liner 114 to cause it to radially flex.

In another possible arrangement (which is not depicted in the accompanying drawings), the first electrode 202 may be formed on or within the teat cup liner 114 itself, as by forming the first electrode 202 as a metallic layer on the liner's exterior surface 126, and/or by forming the first electrode 202 as a conductive network within the body of the teat cup liner 114. In these arrangements, the first electrode 202 is preferably flexible so that it will not hinder the flexure of the teat cup liner 114.

Further advantages, features, and objects of the invention will be apparent from the following detailed description of the invention in conjunction with the associated drawings.

BRIEF DESCRIPTION OF THE DRAWINGS

FIG. 1 is a schematic cross-sectional view of an exemplary version of a conventional teat cup 100, including a teat cup shell 102 and replaceable teat cup liner 114.

FIG. 2 is a schematic cross-sectional view of an exemplary teat cup 200 illustrating principles of the present invention, including a teat cup shell 102 having a first electrode 202 winding about the liner exterior 126, and a second electrode 208 removably inserted within the liner interior 120, with the second electrode 208 being connected to a power supply 222 via a flexible lead 220.

DETAILED DESCRIPTION OF PREFERRED VERSIONS OF THE INVENTION

Referring to FIG. 2, wherein the teat cup 200 is modified from the teat cup 100 of FIG. 1 to present an exemplary version of the invention, a conductive first electrode 202 is situated within the teat cup shell 102, and is configured to closely surround the teat cup liner's exterior surface 126 (more specifically, to surround at least a portion of the exterior surface 126 of the liner barrel 124) as the teat cup liner 114 extends from the teat cup mouth 108 to its extraction end 110. The first electrode 202 is depicted as a coil wound about the exterior surface 126, though it could take other forms, such as a continuous conducting shell surrounding the liner's exterior surface 126. However, since it is desirable to have at least a portion of the liner's exterior surface 126 exposed to the pulsation chamber 106 so that pressure pulses supplied to the pulsation chamber 106 from the pressure supply 112 will flex the liner barrel 124 to massage the teat, a coiled first electrode 202, or other structure wherein the first electrode 202 is formed in spaced sections (here individual windings 204 spaced by apertures 206) to expose the liner's exterior surface 126 to the pulsation chamber 106, is useful. Thus, for example, if the first electrode 202 was instead formed as a continuous shell into which the teat cup liner 114 was fit, it would be useful to define apertures in the shell/first electrode 202 to allow communication of pressure changes to the teat cup liner 114. The configuration of the first electrode 202 may take a wide variety of forms, so long as such configurations cooperate with the second electrode 208 (discussed below) to generate plasma within the teat cup liner 114. It is therefore useful for the first electrode 202 to surround the liner exterior 126 as closely as possible, and it is also useful to define apertures 206 in the first electrode 202 to allow communication of pressure changes from the pulsation chamber 106 to the liner exterior 126. For convenience, the first electrode 202 may be configured as a ground electrode, and thus in FIG. 2 it extends about the teat cup liner 114 to affix to the (conductive) teat cup shell 102, which can be connected to ground.

A second electrode 208, which is usefully defined as an elongated wand-like member extending from a second electrode tip end 210 to a second electrode tail end 212, is removably insertable within the teat cup liner 114. The second electrode 208 is preferably at least partially sheathed in dielectric insulating material 214 (such as a durable ceramic) so that it may be easily handled. Note that while dielectric material 214 is not shown coating the tail end 212 of the second electrode 208, in practice the tail end 212, as well as all other exposed surfaces of the conductive second electrode 208, are usefully covered in some insulating material. The second electrode 208, and/or its dielectric sheath 214, are preferably structured so that at least a substantial portion of its length, when fit within the liner barrel 124 of the teat cup liner 114, will remain spaced from the liner interior surface 122 to define a gap 216 between the outer surface 218 of the second electrode 208 and the liner interior surface 122 in which plasma may be generated. So that the plasma generation gap 216 is easily maintained, the second electrode tip end 210 may be narrowed so that it can be removably received within the liner barrel exit 128, with such insertion maintaining the remainder of the second electrode 208 in a concentric and radially inwardly spaced relationship with respect to the teat cup liner interior surface 122. A lead 220 connects the second electrode tail end 212 to an appropriate power supply 222, with the lead 220 preferably being flexible (and elongated) for ease of maneuvering the second electrode 208, and to allow the user to readily insert and remove the second electrode 208 within the teat cup liner 114 as desired. While only a single electrode 208 is illustrated in FIG. 2, it is expected that in practice, several electrodes 208 will be connected to the power supply 222 so that several teat cups 200 within the same milking cluster may be simultaneously treated. In similar respects, multiple milking clusters may be powered by the same power supply 222 so that several milking clusters may be simultaneously treated within a milking parlor.

By appropriately charging the second electrode 208 (and/or the first electrode 202), plasma will be formed in the gap 216 between the first electrode 202 and the second electrode 208 (more accurately, between the teat cup liner interior surface 122 and the second electrode outer surface 218), thereby treating the teat cup liner interior surface 122. The teat cup 200 has been successfully tested at 10 kV, 7-10 kHz using a 50 W power supply, though a wide variety of other frequencies, voltages, and power levels should work as well, thereby allowing operating conditions to be optimized for specific liner materials. The resulting plasma species will depend heavily upon the type of gas and/or vapor within the gap 216, and assuming standard atmospheric air is within the gap 216, such species will generally be rich in ozone, which has strong disinfectant properties. Since ozone is also corrosive, it can cause degradation of the teat cup liner 114 at its liner interior surface 122; however, rapid degradation is deterred by the thin film of milk that tends to form on the liner interior surface 122 during milking, and degradation can also be reduced by forming the teat cup liner 114 of more ozone-resistant substances such as rubber treated with anti-ozonants, silicone rubber, or other ozone-resistant materials.

Several experiments were performed to test the effectiveness of the teat cup 200. Sterile milk was inoculated with *Streptococcus Uberis* and then poured into conventional rubber teat cup liners 114, which had their milk lines 130 plugged so that the inoculated milk would not flow out. The liners 114 were then hung in an incubator at 37° C. for several hours so the bacteria could multiply and adhere to the interior surfaces 122 of the liners 114. After incubation, the liners 114 were drained and prepared for plasma treatment. In some cases the liners 114 were rinsed with water for approximately 30 seconds prior to treatment; in other cases the rinse was omitted. The interior surface 122 of each liner was swabbed with a bacterial recovery swab (a 3M Quick Swab, 3M, St. Paul, Minn., USA) prior to plasma treatment so that the recovered swab could be tested to obtain a pre-treatment organism count. The liner 114 was then plasma treated in standard atmospheric conditions, i.e., atmospheric air was the process gas present in the plasma gap 216. After treatment, the second electrode 208 was removed, and a different area of the treated liner 114 having the same size was swabbed to obtain post-treatment organism counts. This procedure was repeated for each liner 114. The swabs were plated onto TSA II agar with 5% sheep blood and allowed to incubate at 37° C. for approximately 24 hours. The plates were then read to obtain bacteria counts. In many cases, especially in plates from pretreatment swabs, bacteria counts were too high to enumerate and are recorded as TNTC (Too Numerous To Count).

The first experiment used teat cup liners 114 obtained from previous experiments, and results are set forth in TABLE 1. In this case a contaminant organism was present in many of the plates. This organism is believed to be a *Pseudomonas*, and was probably present on the liners before the experiment began.

TABLE 1

| | Experimental Conditions | | | Results | |
| --- | --- | --- | --- | --- | --- |
| Trial # | Water rinse of liner prior to plasma treatment? | Treatment time | Power (W) | Bacteria count before treatment (CFU/ml) | Bacteria count after treatment (CFU/ml) |
| 1 | No | 2 min | 50 | TNTC | 0 |
| 2 | No | 2 min | 50 | TNTC | 1 |
| 3 | No | 1 min | 50 | TNTC | TNTC |
| 4 | No | 30 sec | 50 | hundreds | TNTC |
| 5 | No | 15 sec | 50 | hundreds | TNTC |
| 6 | Yes | 2 min | 50 | hundreds | 10 |
| 7 | Yes | 2 min | 50 | hundreds | 0 |
| 8 | Yes | 1 min | 50 | hundreds | 7 |
| 9 | Yes | 30 sec | 50 | hundreds | 250 |
| 10 | Yes | 15 sec | 50 | hundreds | about 100 |

In this experiment, the pretreatment swabs used a 1:50 dilution. Thus, plates that are TNTC might still be estimated to have 1,000 CFU/ml, yet in this case we multiply by 50 (100*50-50,000) to yield a better estimate of the level of pretreatment contamination. The results appear to indicate that longer treatment times leads to greater reduction in bacteria counts.

The second set of experiments used liners that had been used under regular milking conditions at the Dairy Cattle Center, also at the University of Wisconsin-Madison. To reduce the probability of contaminant organisms, the liners 114 were thoroughly washed with detergent and rinsed with water prior to use in the experiment. Results are reflected in TABLE 2:

TABLE 2

| | Experimental Conditions | | | Results | |
|---|---|---|---|---|---|
| Trial # | Water rinse of liner prior to plasma treatment? | Treatment time | Power (W) | Bacteria count before treatment (CFU/ml) | Bacteria count after treatment (CFU/ml) |
| 1 | Yes | 2 min | 50 | Error in plating - no data | Error in plating - no data |
| 2 | Yes | 1 min | 50 | TNTC | 21 |
| 3 | Yes | 1 min | 50 | TNTC | 65 |
| 4 | Yes | 2 min | 50 | 2500 | 0 |
| 5 | Yes | 30 sec | 50 | TNTC | 230 |
| 6 | Yes | 30 sec | 50 | 16250 | 4800 |

Again, in this case a 1:50 dilution was used for pretreatment swab solutions. Plates that were TNTC would be estimated to have at least 1000*50-50,000 CFU/ml. Again, the results indicate that longer treatment time leads to greater reduction in bacteria counts.

In summary, the experiments illustrate that plasma treatment can greatly decrease organism counts within the liners 114, particularly where more extended treatment times are used. It is expected that if greater field strengths are used, the same or greater degree of disinfection might occur with decreased treatment times.

To summarize the operation of the teat cup 200 of FIG. 2, the teat cup 200 may (with the second electrode 208 removed) be used in standard fashion to extract milk from a teat. Once the teat is removed, the teat cup 200 may be disinfected prior to its use on a subsequent cow by inserting the second electrode 208 as depicted in FIG. 2, and activating the power supply 222 so that plasma is formed within the gap 216. Once plasma disinfection has occurred for the desired period of time, the second electrode 208 may be removed (preferably after disabling the power supply 222 or otherwise setting the potential of the second electrode 208 to ground), and the teat cup 200 may then be used on a subsequent cow in standard fashion. The teat cup 200 should be useful in destroying common mastitis-causing bacteria, such as *Streptococcus agalactiae, Staphylococcus aureus*, and *Corynebacterium bovis*, as well as common environmental bacteria (e.g., those commonly found in bedding material and feces, such as streptococci, enterococci, and coliforms) which may contaminate milk, or which may also cause mastitis or other conditions. It is expected that the milking machine may be particularly useful in destroying hardy organisms that are resistant to antibiotics and other treatments, such as *Pseudomonas aeruginosa, Actinomyces pyogenes*, and *Mycoplasma bovis*, which at this time can usually only be eliminated by culling infected cows from the herd.

It should be understood that an exemplary preferred version of the invention has been described above, and numerous modifications are considered to be within the scope of the invention. Following is an exemplary list of such modifications.

First, rather than implementing the invention in a conventional milking machine, it is instead possible to develop new milking machines which are specifically adapted to implement the invention. For example, a teat cup liner 114 can be formed with an embedded first electrode 202, or with a metallized outer surface or adhered outer winding which serves as the first electrode 202, so that the first electrode 202 is insertable and removable with the liner. Alternatively, the first electrode 202 could be formed by, or as a part of, the teat cup shell 102 itself. However, in this case, it must be kept in mind that plasma generation may occur in any gas and/or vapor-filled free space between the first and second electrodes 202 and 208, and thus plasma generation might occur between the teat cup shell 102 and the exterior surface 126 of the teat cup liner 114 (and plasma generation at this space may not be useful or desirable). Further, the efficiency of plasma generation decreases as the spacing between the first and second electrodes 202 and 208 increases, and thus having a conventional teat cup shell 102 serve as the first electrode 202 may decrease results. Thus, if the first electrode 202 is defined by the teat cup shell 102, it might be useful to have the teat cup shell 102 include projections extending from its interior surface 104 toward the exterior surface 126 of the teat cup liner 114, and which receive the teat cup liner 114 and define the first electrode 202.

Second, the teat cup 200 may be used in conjunction with compatible backflush or other cleaning systems, which might complement the cleaning/disinfecting action of the teat cup 200. As an example, the teat cup liner 114 might be fitted with a system which introduces water and/or compressed air to better flush any heavy organic matter (e.g., mud, feces) from the liner interior surface 122.

Third, the teat cup 200 can be adapted to generate specific desired plasma species. When standard atmospheric air is used as the process gas within the plasma gap 216, the primary resulting plasma species is believed to be ozone. If desired, other special plasma species may be generated within the plasma gap 216 by providing different and/or additional process gases within the gap 216 during treatment. Such an arrangement might by accommodated, for example, by providing a gas supply line to the second electrode 208 in addition to the electrical lead 220, and having the gas supply line open onto the second electrode outer surface 218, and thus open onto the liner interior 120 when the second electrode 208 is inserted within the teat cup liner 114. Prior to activation of the power supply 222, a small burst of an additional and/or different process gas might be injected through the supply line into the liner interior 120 so that this process gas is provided within the plasma gap 216 during treatment. If the gas supply line opens onto the outer surface 218 of the second electrode 208 at such a point that the injected gas enters the liner interior 120 near the liner's barrel exit 128, the supply gas might even displace the existing atmospheric air through the liner's liner mouth 118, resulting in little or no atmospheric air within the liner interior 120 and plasma gap 216 during treatment.

Fourth, the plasma gap 216 may be created and maintained by means other than by having the second electrode tip end 210 insert into the liner barrel exit 128. As an example, the outer surface 218 of the second electrode 208 may bear nubs or other extensions which protrude radially outwardly to engage the interior surface 122 of the liner 114, so that a major portion of the liner's exterior surface 126 is maintained in spaced relationship from the second electrode 208. Alternatively and/or additionally, the second electrode 208 might bear some structure at or near its tail end 212 which engages the mouth end 116 of the teat cup liner 114 to hold the second electrode 208 in coaxially spaced relationship with respect to the teat cup liner 114.

Fifth, the first electrode 202 need not wrap solely about the liner barrel 124 of the liner 114, and it might additionally (or alternatively) extend about surfaces of the teat cup liner 114 at the teat cup mouth 108 to provide disinfection about the liner's liner mouth 118. As another option, the first electrode 202 might extend about at least a portion of the liner's milk line 130 (in which case the tip end 210 of the second electrode 208 may need to be configured to define a plasma gap 216 within the milk line 130 for effective treatment). Additionally, the electrodes 202 and 208 might be configured so as to concentrate plasma generation in areas of the liner 114 which have a higher probability of organism accumulation, as by configuring such areas with narrower plasma generation gaps 216 and/or greater electrode density (e.g., by more tightly spaced electrode sections 204 or reduced/eliminated apertures 206 in the first electrode 202).

Sixth, it may also be possible to avoid the use of an insertable second electrode 208, and instead provide both the first and second electrodes 206 and 208 about the exterior surface 126 of the liner 114 (preferably spaced solely by dielectric material, with no free space therebetween). With sufficient electric field strength, such an arrangement may generate an effective amount of plasma within the liner interior 120, even though no portion of the liner interior 120 rests directly between the electrodes. However, the use of electrodes 202 and 208 spaced by dielectric material next to a free space (here the liner interior 120) may require a more robust power supply 222 to result in an effective amount of plasma generation, and the spacing and configuration of the electrodes may need to be carefully planned to optimize plasma generation.

Finally, it should be understood that while the foregoing discussion was cast in terms of the use of the invention in the milking of cows, it is also usable in the milking of other animals as well.

The invention is not intended to be limited to the preferred versions of the invention described above, but rather is intended to be limited only by the claims set out below. Thus, the invention encompasses all different versions that fall literally or equivalently within the scope of these claims.

What is claimed is:

1. A milking machine comprising:
    a. a teat cup sized to receive a teat therein;
    b. a first electrode situated within the teat cup, the first electrode having a concave interior sized to receive a teat inserted within the teat cup;
    c. a second electrode situated within the teat cup, the second electrode not being in conductive communication with the first electrode and being spaced therefrom, with dielectric material blocking the space between the first and second electrode;
    d. a power supply connected to at least one of the first and second electrodes, the power supply being capable of charging at least one of the electrodes to induce the electrodes to generate plasma so as to at least partially disinfect an area within the teat cup.

2. The milking machine of claim 1 wherein the second electrode is removably insertable within the teat cup, and also within any teat cup liner therein.

3. The milking machine of claim 1 wherein:
    a. the second electrode is formed as an elongated member extending from a tip end to a tail end, and
    b. at least the tip end is surrounded by dielectric material.

4. The milking machine of claim 3 wherein a flexible conductive lead extends from the second electrode at or adjacent to its tail end.

5. The milking machine of claim 1 wherein the first electrode includes several spaced first electrode sections, whereby pressure changes within the interior of the teat cup are communicated between the first electrode sections.

6. The milking machine of claim 1 wherein the first electrode includes apertures defined therein, the apertures allowing pressure changes about the exterior of the first electrode to be communicated to the interior of the first electrode.

7. The milking machine of claim 1 further comprising a teat cup liner removably inserted within the interior of the first electrode.

8. The milking machine of claim 7 wherein:
    a. the second electrode is formed as an elongated member;
    b. the teat cup liner has a concave interior surface wherein at least a portion of the second electrode is situated;
    c. one portion of the length of the second electrode engages the teat cup liner to maintain another portion of the length of the second electrode spaced radially inwardly from the interior surface of the teat cup liner.

9. The milking machine of claim 1 further comprising a teat cup liner removably inserted within the teat cup, wherein the first electrode is provided on or within the teat cup liner.

10. A milking machine comprising:
    a. a first electrode having a body surrounding an at least substantially cylindrical first electrode interior, the first electrode interior extending between:
        (1) a drain end, and
        (2) an open receiving end sized to receive a teat within the first electrode interior;
    b. a second electrode removably insertable within the first electrode interior;
    c. a milk communication line extending away from the drain end of the first electrode;

wherein the first and second electrodes are chargeable with respect to each other to generate plasma therebetween so as to at least partially disinfect an area between the first and second electrodes.

11. The milking machine of claim 10:
a. further comprising a teat cup situated about the first electrode, and
b. wherein the milk communication line leads from a flexible teat cup liner situated within the teat cup, wherein the first electrode is provided about or within the teat cup liner.

12. The milking machine of claim 11 wherein the milk communication line extends from the teat cup liner.

13. The milking machine of claim 10 wherein the first electrode includes several spaced first electrode sections, whereby changes in pressure about the exterior of the first electrode are communicated to the interior of the first electrode.

14. The milking machine of claim 10 wherein the first electrode includes apertures defined therein, the apertures allowing pressure changes about the exterior of the first electrode to be communicated to the interior of the first electrode.

15. The milking machine of claim 10 wherein:
a. the second electrode is configured as an elongated member extending from a tip end to a tail end, and
b. a conductive lead extends from the second electrode at or adjacent to its tail end.

16. The milking machine of claim 10 wherein the second electrode has an exterior which is at least partially covered by dielectric material.

17. A milking machine comprising:
a. a first electrode configured to closely surround at least a portion of the exterior of a teat cup liner;
b. a second electrode removably insertable within the interior of the teat cup liner;
c. a power supply connected to at least one of the first and second electrodes, the power supply being capable of charging at least one of the electrodes to generate plasma between the electrodes so as to at least partially disinfect an area between the electrodes.

18. The milking machine of claim 17 wherein:
a. the second electrode extends from a tip to a tail, and
b. at least the tip is surrounded by dielectric material, the surrounded tip being removably insertable within the interior of the teat cup liner.

19. The milking machine of claim 18 further comprising a flexible conductive lead extending from the second electrode at or near its tail.

20. The milking machine of claim 17 wherein the first electrode is situated within a teat cup wherein the teat cup liner is removably inserted.

21. The milking machine of claim 20 wherein:
a. the teat cup has a pressure supply connected thereto, and
b. the first electrode has apertures defined therein allowing pressure changes from the pressure supply to be communicated through the apertures to the teat cup liner.

22. The milking machine of claim 17 wherein:
a. the first electrode includes several first electrode sections which closely surround at least a portion of the exterior of the teat cup liner, and
b. the first electrode sections are spaced to leave portions of the teat cup liner unsurrounded.

23. A method of disinfecting a milking machine having a teat cup liner, the method comprising the steps of:
a. providing a first electrode which closely surrounds at least a portion of the exterior of the teat cup liner;
b. inserting a second electrode within the interior of the teat cup liner; and
c. charging at least one of the electrodes to generate plasma between the electrodes so as to at least partially disinfect the teat cup liner.

24. The milking machine of claim 1 wherein the first electrode and second electrode bear different charges.

25. The milking machine of claim 1 wherein one of the first electrode and the second electrode is situated within the other.

* * * * *